United States Patent
Jang

(10) Patent No.: US 10,393,776 B2
(45) Date of Patent: Aug. 27, 2019

(54) REPRESENTATIVE WAVEFORM PROVIDING APPARATUS AND METHOD

(71) Applicant: SAMSUNG ELECTRONICS CO., LTD., Suwon-si (KR)

(72) Inventor: Dae Geun Jang, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 15/471,225

(22) Filed: Mar. 28, 2017

(65) Prior Publication Data
US 2018/0128861 A1 May 10, 2018

(30) Foreign Application Priority Data
Nov. 7, 2016 (KR) .................. 10-2016-0147601

(51) Int. Cl.
| | |
|---|---|
| G01R 17/02 | (2006.01) |
| G01R 19/00 | (2006.01) |
| A61B 5/00 | (2006.01) |
| A61B 5/1455 | (2006.01) |
| G16H 50/30 | (2018.01) |

(52) U.S. Cl.
CPC ............ *G01R 17/02* (2013.01); *A61B 5/1455* (2013.01); *A61B 5/7246* (2013.01); *A61B 5/7275* (2013.01); *G01R 19/003* (2013.01); *G16H 50/30* (2018.01)

(58) Field of Classification Search
None
See application file for complete search history.

(56) References Cited

U.S. PATENT DOCUMENTS

| | | | |
|---|---|---|---|
| 4,467,437 A * | 8/1984 | Tsuruta | ............... G06K 9/6206 382/215 |
| 5,926,050 A * | 7/1999 | Proebsting | ......... H03K 19/0013 326/17 |
| 7,245,960 B2 | 7/2007 | Yasushi et al. | |
| 8,010,362 B2 | 8/2011 | Tamura et al. | |
| 8,140,334 B2 | 3/2012 | Jeong et al. | |
| 8,290,575 B2 | 10/2012 | Tarassenko et al. | |
| 8,306,939 B2 | 11/2012 | Katoaka | |
| 8,548,612 B2 | 10/2013 | Rhein | |

(Continued)

FOREIGN PATENT DOCUMENTS

| | | |
|---|---|---|
| JP | 5178471 B2 | 4/2013 |
| KR | 10-0304665 B1 | 9/2001 |
| KR | 10-2015-0052556 A | 5/2015 |
| KR | 10-1578167 B1 | 12/2015 |
| KR | 10-1587874 B1 | 1/2016 |
| KR | 10-2016-0026496 A | 3/2016 |

OTHER PUBLICATIONS

Ghazi Al-Naymat, Sparse DTW: A Novel Approach to Speed up Dynamic Time Warping, Jan. 13, 2012, p. 1-17. <<https://arxiv.org/pdf/1201.2969.pdf>>.*

(Continued)

*Primary Examiner* — Tung S Lau
(74) *Attorney, Agent, or Firm* — Sughrue Mion, PLLC

(57) ABSTRACT

A representative waveform providing apparatus and method, a blood pressure estimation apparatus, and a wearable device are provided. The representative waveform providing apparatus may include a signal obtainer configured to obtain a periodic signal and a processor configured to determine a representative waveform of the periodic signal by using a dynamic time warping algorithm.

19 Claims, 11 Drawing Sheets

(56) References Cited

U.S. PATENT DOCUMENTS

| | | |
|---|---|---|
| 8,853,516 B2 | 10/2014 | Arimoto et al. |
| 9,189,198 B2 | 11/2015 | Otani et al. |
| 2004/0260552 A1* | 12/2004 | Navratil ................. G10L 15/07 704/269 |
| 2010/0026479 A1* | 2/2010 | Tran ..................... A61B 5/0006 340/501 |
| 2011/0077758 A1* | 3/2011 | Tran ....................... G16H 40/67 700/94 |
| 2012/0232838 A1* | 9/2012 | Kemppi ................. G01C 17/28 702/150 |
| 2012/0323521 A1 | 12/2012 | De Foras et al. |
| 2013/0024029 A1* | 1/2013 | Tran ....................... G16H 50/20 700/278 |
| 2013/0144611 A1* | 6/2013 | Ishikawa ................ G10L 25/90 704/207 |
| 2013/0190008 A1* | 7/2013 | Vathsangam ........... H04M 1/00 455/456.1 |
| 2016/0055316 A1* | 2/2016 | Jafari .................. G06F 19/3456 340/573.1 |
| 2016/0063233 A1 | 3/2016 | Bae et al. |

OTHER PUBLICATIONS

Muhammad Ali Shami in Morphable DPU: Smart and Efficient Data Path for Signal Processing Applications, 2009 IEEE, pp. 167-172.*

Samaneh Ghandali in RTL Datapath Optimization Using System-level Transformations, 8 pages, IEEE 2014.*

Salvador, et al., "FastDTW: Toward Accurate Dynamic Time Warping in Linear Time and Space", 2004, KDD Workshop on Mining Temporal and Sequential Data, 11 pages total.

Al-Naymat, et al., "SparseDTW: A Novel Approach to Speed up Dynamic Time Warping", 2009, Proc. of the 8th Australasian Data Mining Conference, vol. 101, pp. 117-127.

Silva, et al., "Speeding Up All-Pairwise Dynamic Time Warping Matrix Calculation", 2015, 9 pages total.

Anonymous, "Dynamic time warping", Wikipedia, Mar. 17, 2017, 5 pages total https://en.wikipedia.org/wiki/Dynamic_time_warping.

\* cited by examiner

REPRESENTATIVE WAVEFORM PROVIDING APPARATUS AND METHOD

CROSS-REFERENCE TO RELATED APPLICATION(S)

This application claims priority from Korean Patent Application No. 10-2016-0147601, filed on Nov. 7, 2016, in the Korean Intellectual Property Office, the disclosure of which is incorporated herein in its entirety by reference.

BACKGROUND

1. Field

Apparatuses and methods consistent with exemplary embodiments relate to a technology of determining and providing a representative waveform of a quasi-periodic signal.

2. Description of Related Art

Healthcare technology has attracted much attention due to the rapid entry into an aging society and relevant problems such as increase in medical expenses. Accordingly, not only medical devices that can be utilized by hospitals and inspection agencies but also small-sized medical devices that can be carried by individuals such as wearable devices are being developed. In addition, such a small-sized medical device is worn by a user in the form of a wearable device capable of measuring the user's health condition, such as blood pressure or the like, so that the user can measure and manage his/her health condition.

Bio-signal analysis is carried out by analyzing a representative waveform that represents the bio-signal. Thus, the determination of a representative waveform of a bio-signal is related to the accuracy of the bio-signal analysis.

Since a bio-signal has a quasi-periodic characteristic in which the period gradually changes with time, a method of determining a representative waveform of a quasi-periodic bio-signal is needed.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an exemplary embodiment, there is provided a representative waveform providing apparatus including a signal obtainer configured to obtain a periodic signal and a processor configured to determine a representative waveform of the periodic signal by using a dynamic time warping (DTW) algorithm.

The periodic signal may include a periodic signal whose period does not change over time and a substantially periodic signal whose period gradually changes with time.

The processor may include a signal segmentator configured to generate a plurality of periodic signal segments by segmenting the periodic signal according to periods, a similarity determiner configured to determine a similarity of the plurality of periodic signal segments to each other using the DTW algorithm, and a representative waveform determiner configured to determine the representative waveform of the periodic signal based on a result of determining the similarity.

The similarity determiner may determine the similarity of the plurality of periodic signal segments to each other by using a method which time-synchronizes each pair of two periodic signal segments by applying the DTW algorithm to the two periodic signal segments in each pair and determine the similarity between the two time-synchronized periodic signal segments in each pair.

The similarity determiner may determine the similarity between the time-synchronized two periodic signal segments by using at least one of correlation, signal difference, and an accumulated distance of an optimal path obtained in the process of time-synchronization.

The representative waveform determiner may determine the representative waveform based on a periodic signal segment having a highest similarity to other periodic signal segments among the plurality of periodic signal segments.

The representative waveform determiner may select a predetermined number of periodic signal segments having high similarities to other periodic signal segments from among the plurality of periodic signal segments, obtain an ensemble average of the selected periodic signal segments, and determine the representative waveform based on the obtained ensemble average.

The representative waveform determiner may select two or more periodic signal segments whose similarities to other periodic signal segments are greater than a predetermined threshold from among the plurality of periodic signal segments, obtain an ensemble average of the two or more selected periodic signal segments, and determine the representative waveform based on the obtained ensemble averaged.

The processor may include an interval divider configured to divide the periodic signal into predetermined time intervals, a signal segmentator configured to generate a plurality of periodic signal segments for each time interval by segmenting the periodic signal in each time interval according to periods, a similarity determiner configured to determine a similarity of the plurality of periodic signal segments to each other in each time interval using the DTW algorithm, and a representative waveform determiner configured to determine a signal quality of each time interval based on a result of determining the similarity and determine the representative waveform of the periodic signal based on results of determining the signal quality and the similarity.

The representative waveform determiner may determine that a signal quality of a time interval is higher in response to determining that a similarity of the plurality of periodic signal segments to each other in the corresponding time interval is higher.

The representative waveform determiner may determine the representative waveform based on a periodic signal segment having a highest similarity to other periodic signal segments among the plurality of periodic signal segments in a time interval having a highest signal quality.

The representative waveform determiner may select one periodic signal segment having a highest similarity to other periodic signal segment from among the periodic signal segments for each time interval, ensemble average the selected periodic signal segments of each time interval to obtain an ensemble-averaged signal, and determine the representative waveform based on the ensemble-averaged signal.

The representative waveform determiner may ensemble average the selected periodic signal segments by applying a different weight to the periodic signal segment selected for each time interval according to a signal quality of each time interval.

In another aspect, there is provided a representative waveform providing method including obtaining a periodic signal and determining a representative waveform of the periodic signal by using a dynamic time warping (DTW) algorithm.

The determining of the representative waveform of the periodic signal may include generating a plurality of periodic signal segments by segmenting the periodic signal according to periods, determining a similarity of the plurality of periodic signal segments to each other using the DTW algorithm, and determining the representative waveform of the periodic signal based on a result of determining the similarity.

The determining of the representative waveform of the periodic signal may include determining the representative waveform based on a periodic signal segment having a highest similarity to other periodic signal segments among the plurality of periodic signal segments.

The determining of the representative waveform of the periodic signal may include selecting a predetermined number of periodic signal segments having high similarities to other periodic signal segments from among the plurality of periodic signal segments, obtaining an ensemble average of the selected periodic signal segments to obtain an ensemble-averaged signal, and determining the representative waveform based on the obtained ensemble-averaged signal.

The determining of the representative waveform of the periodic signal may include selecting two or more periodic signal segments whose similarities to other periodic signal segments are greater than a predetermined threshold from among the plurality of periodic signal segments, obtaining an ensemble average of the two or more selected periodic signal segments to obtain an ensemble-averaged signal, and determining the representative waveform based on the obtained ensemble-averaged signal.

The determining of the representative waveform of the periodic signal may include dividing the periodic signal into predetermined time intervals, generating a plurality of periodic signal segments for each time interval by segmenting the periodic signal in each time interval according to periods, determining a similarity of the plurality of periodic signal segments to each other in each time interval using the DTW algorithm, determining a signal quality of each time interval based on a result of determining the similarity, and determining the representative waveform of the periodic signal based on results of determining the signal quality and the similarity.

The determining of the representative waveform of the periodic signal based on results of determining the signal quality and the similarity may include determining the representative waveform based on a periodic signal segment having a highest similarity to other periodic signal segments among the plurality of periodic signal segments in a time interval having a highest signal quality.

The determining of the representative waveform of the periodic signal based on results of determining the signal quality and the similarity may include selecting one periodic signal segment having a highest similarity to other periodic signal segment from among the periodic signal segments for each time interval, ensemble averaging the selected periodic signal segments by applying a different weight to the periodic signal segment selected for each time interval according to a signal quality of each time interval, and determining the representative waveform based on the ensemble-averaged signal.

Other features and aspects will be apparent from the following detailed description, the drawings, and the claims.

BRIEF DESCRIPTION OF THE DRAWINGS

The above and/or other aspects will be more apparent by describing certain exemplary embodiments with reference to the accompanying drawings.

DETAILED DESCRIPTION

Figure 1:
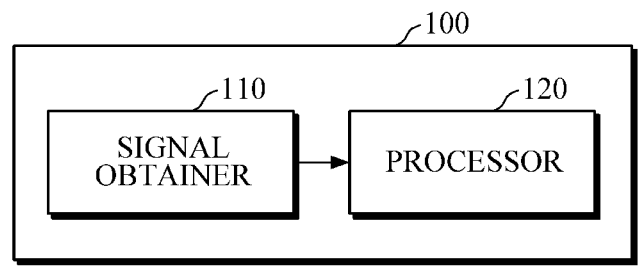
FIG. 1 is a block diagram illustrating an exemplary embodiment of a representative waveform providing apparatus.

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail.

Throughout the drawings and the detailed description, unless otherwise described, the same drawing reference numerals will be understood to refer to the same elements, features, and structures. The relative size and depiction of these elements may be exaggerated for clarity, illustration, and convenience.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described in below are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

FIG. 1 is a block diagram illustrating an exemplary embodiment of a representative waveform providing apparatus. The representative waveform providing apparatus 100 shown in FIG. 1 may be implemented as a software module, a hardware module, and/or a combination thereof. For example, the representative waveform providing apparatus 100 may be provided in the form of a hardware chip and mounted on an electronic device. In this case, the electronic device may include a mobile phone, a smart phone, a notebook computer, a personal digital assistant (PDA), a portable multimedia player (PMP), a navigation system, an MP3 player, a digital camera, a wearable device, etc., and the wearable device may include various types of wearable devices, such as a wristwatch type, a wristband type, a ring type, a belt-type, a necklace type, an ankle band type, a thigh band type, a forearm band type, and the like. However, the electronic device is not limited to the above mentioned examples, and the wearable device is also not limited to the above-described examples.

Referring to FIG. 1, the representative waveform providing apparatus 100 includes a signal obtainer 110 and a processor 120.

The signal obtainer 110 may obtain a periodic signal. Here, the periodic signal may include a periodic signal whose period does not change over time and a substantially periodic signal whose period gradually changes with time. For example, the periodic signal may include a photoplethysmogram (PPG) signal, an electrocardiogram (ECG) signal, a ballistocardiogram (BCG) signal, and the like, but is not limited thereto.

According to an exemplary embodiment, the signal obtainer 110 may obtain a periodic signal from an external device which senses and/or stores periodic signals. In this case, the signal obtainer 110 may use various communication technologies, such as Bluetooth communication, Bluetooth low energy (BLE) communication, near-field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, 5G communication, or the like.

According to another exemplary embodiment, the signal obtainer 110 may include various sensors, such as a PPG sensor, an ECG sensor, a BCG sensor, and the like, which senses a periodic signal, and may obtain the periodic signal through the sensors.

The processor 120 may determine a representative waveform of the periodic signal by using a dynamic time warping (DTW) algorithm. In this case, the representative waveform may refer to a signal that may best represent the characteristics of the periodic signal.

Hereinafter, various exemplary embodiments of the processor 120 will be described in detail with reference to FIGS. 2 and 3.

Figure 2:
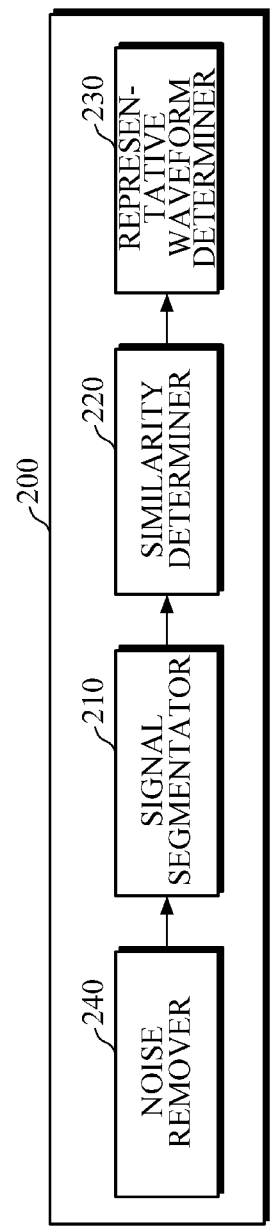
FIG. 2 is a block diagram illustrating an exemplary embodiment of a processor of a representative waveform providing apparatus.

FIG. 2 is a block diagram illustrating an exemplary embodiment of a processor. The processor 200 of FIG. 2 may be an exemplary embodiment of the processor 120 of FIG. 1.

Referring to FIG. 2, the processor 200 includes a signal segmentator 210, a similarity determiner 220, and a representative waveform determiner 230.

The signal segmentator 210 may generate a plurality of periodic signal segments by segmenting the periodic signal according to periods.

The similarity determiner 220 may determine a similarity of the periodic signal segments to each other using the DTW algorithm. According to an exemplary embodiment, the similarity determiner 220 may determine the similarity of the plurality of periodic signal segments to each other using a method which time-synchronizes each pair of two periodic signal segments by applying the DTW algorithm to the two periodic signal segments in each pair to maximize the similarity between the two periodic signal segments and determines the similarity between the two time-synchronized periodic signal segments in each pair. In this case, the similarity determiner 220 may determine the similarity between the two time-synchronized periodic signal segments by using at least one of correlation, signal difference, and an accumulated distance of an optimal path obtained in the process of time-synchronization.

A method of time-synchronization of two periodic signal segments using the DTW algorithm will be described below in detail with reference to FIG. 4.

The representative waveform determiner 230 may determine a representative waveform based on the similarity of the plurality of periodic signal segments to each other.

According to an exemplary embodiment, the representative waveform determiner 230 may select one periodic signal segment having the highest similarity to other periodic signal segments and may determine the selected periodic signal segment as the representative waveform. In this case, a degree of similarity may be determined based on an average of similarities to other periodic signal segments.

According to another exemplary embodiment, the representative waveform determiner 230 may select a predetermined number of periodic signal segments having high similarities to other periodic signal segments from among the plurality of periodic signal segments, obtain an ensemble average of the selected periodic signal segments to obtain an ensemble-averaged signal, and determine the obtained ensemble-averaged signal as the representative waveform.

According to still another exemplary embodiment, the representative waveform determiner 230 may select two or more periodic signal segments whose similarities to other periodic signal segments are greater than a predetermined threshold from among the plurality of periodic signal segments, obtain an ensemble average of the two or more selected periodic signal segments to obtain an ensemble-averaged signal, and determine the obtained ensemble-averaged signal as the representative waveform.

The processor 200 may optionally include a noise remover 240 to remove noise from the periodic signal.

Figure 3:
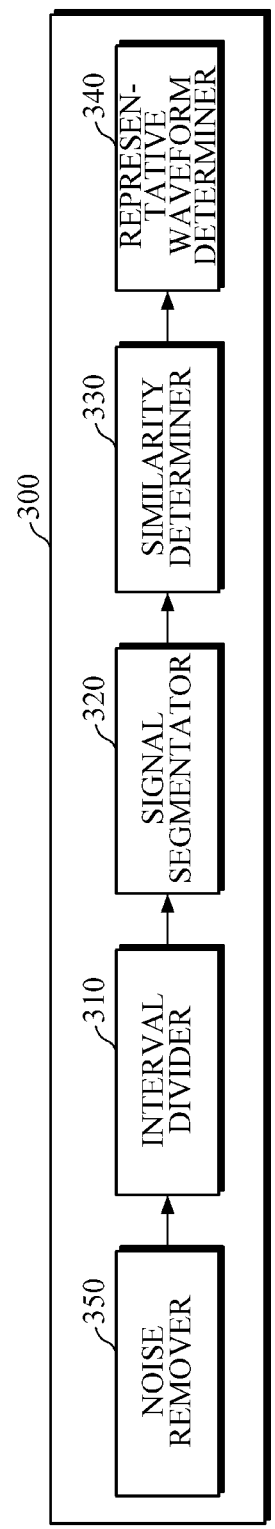
FIG. 3 is a block diagram illustrating another exemplary embodiment of a processor of a representative waveform providing apparatus.

FIG. 3 is a block diagram illustrating another exemplary embodiment of a processor. The processor 300 of FIG. 3 may be another exemplary embodiment of the processor 120 of FIG. 1.

Referring to FIG. 3, the processor 300 includes an interval divider 310, a signal segmentator 320, a similarity determiner 330, and a representative waveform determiner 340.

The interval divider 310 may divide a periodic signal into predetermined time intervals.

The signal segmentator 320 may segment the periodic signal in each time interval according to periods and generate a plurality of periodic signal segments for each time interval.

The similarity determiner 330 may determine a similarity of the periodic signal segments to each other of each time interval using a DTW algorithm. According to an exemplary embodiment, the similarity determiner 330 may determine the similarity of the plurality of periodic signal segments to each other using a method which time-synchronizes each pair of two periodic signal segments by applying the DTW algorithm to the two periodic signal segments in each pair to maximize the similarity between the two periodic signal segments and determines the similarity between the two time-synchronized periodic signal segments in each pair. In this case, the similarity determiner 330 may determine the similarity between the two time-synchronized periodic signal segments by using at least one of correlation, signal difference, and an accumulated distance of an optimal path obtained in the process of time-synchronization.

The representative waveform determiner 340 may determine a quality of a periodic signal of each time interval based on the similarity of the periodic signal segments to each other in each time interval. For example, the representative waveform determiner 340 may determine that the quality of the periodic signal of a specific time interval is high when the similarity among the periodic signal segments of the corresponding time interval is high and determine that the quality of the periodic signal of a time interval is low when the similarity among the periodic signal segments of the corresponding time interval is low.

The representative waveform determiner 340 may determine the representative waveform of the periodic signal based on the signal quality determination result of each time interval and the similarity of the periodic signal segments to each other in each time interval.

According to an exemplary embodiment, the representative waveform determiner 340 may select a time interval having the highest signal quality, select one periodic signal segment having the highest similarity to other periodic signal segments from among the periodic signal segments of the selected time interval, and determine the selected periodic signal segment as the representative waveform.

According to another exemplary embodiment, the representative waveform determiner 340 may select a time interval having the highest signal quality, select a predetermined number of periodic signal segments having high similarities to other periodic signal segments from among the periodic signal segments in the selected time interval, ensemble average the selected periodic signal segments to obtain an ensemble-averaged signal, and determine the obtained ensemble-averaged signal as the representative waveform.

According to still another exemplary embodiment, the representative waveform determiner 340 may select a time interval having the highest signal quality, select two or more periodic signal segments whose similarities to other periodic signal segments are greater than a predetermined threshold from among the periodic signal segments in the selected time interval, ensemble average the two or more selected periodic signal segments to obtain an ensemble-averaged signal, and determine the obtained ensemble-averaged signal as the representative waveform.

According to yet another exemplary embodiment, the representative waveform determiner 340 may select one periodic signal segment having the highest similarity to other periodic signal segment from among the periodic signal segments for each time interval, ensemble average the selected periodic signal segments of each time interval to obtain an ensemble-averaged signal, and determine the ensemble-averaged signal as the representative waveform. In this case, the representative waveform determiner 340 may apply a different weight to the periodic signal segment selected for each time interval according to a signal quality of each time interval.

The processor 300 may optionally include a noise remover 350 to remove noise from the periodic signal.

Figure 4:
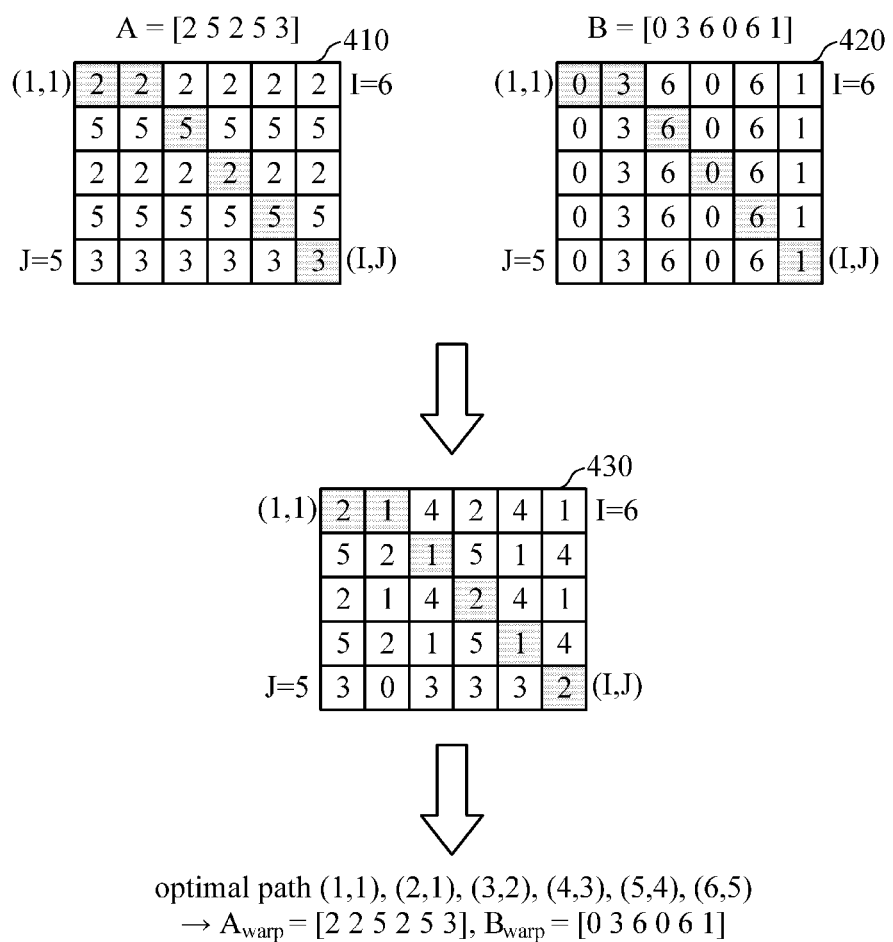
FIG. 4 is a diagram for describing a method of time-synchronizing two periodic signal segments using a dynamic time warping (DTW) algorithm.

FIG. 4 is a diagram for describing a method of time-synchronizing two periodic signal segments using a DTW algorithm according to an exemplary embodiment.

Referring to FIGS. 2 and 4, the similarity determiner 220 generates matrix A 410 based on periodic signal segment A [2 5 2 5 3], wherein the matrix A 410 includes six column vectors corresponding to the number of data of periodic signal segment B [0 3 6 0 6 1], and each column vector has data of periodic signal segment A.

The similarity determiner 220 generates matrix B 420 based on periodic signal segment B [0 3 6 0 6 1], wherein the matrix B 420 has five row vectors corresponding to the number of data of periodic signal segment A [2 5 2 5 3], and each row vector has data of periodic signal segment B.

The similarity determiner 220 generates new matrix C 430 by calculating a distance (e.g., Euclidean distance or the like) between matrix A 410 and matrix B 420.

The similarity determiner 220 may search in a direction (e.g., right, down, right-down) from (1,1) of matrix C 430 to find an optimal path comprising (1,1), (2,1), (3,2), (4,3), (5,4), (6,5) that has a minimum accumulated distance.

The similarity determiner 220 generates a periodic signal segment $A_{warp}$ [2 2 5 2 5 3] and a periodic signal segment $B_{warp}$ [0 3 6 0 6 1] which are time-synchronized with each other using the found optimal path (1,1), (2,1), (3,2), (4,3), (5,4), (6,5) so that a similarity between the periodic signal segment A and the periodic signal segment B is maximized.

The similarity determiner 220 may determine the similarity between the periodic signal segment A and the periodic signal segment B by determining the similarity between the time-synchronized periodic signal segment $A_{warp}$ and the time-synchronized periodic signal segment $B_{warp}$. In this case, the similarity determiner 220 may determine the similarity between the periodic signal segment A and the periodic signal segment B by using at least one of the correlation, signal difference, and an accumulated distance (e.g., 9 in matrix C430) obtained in the process of time-synchronization.

Figure 5:
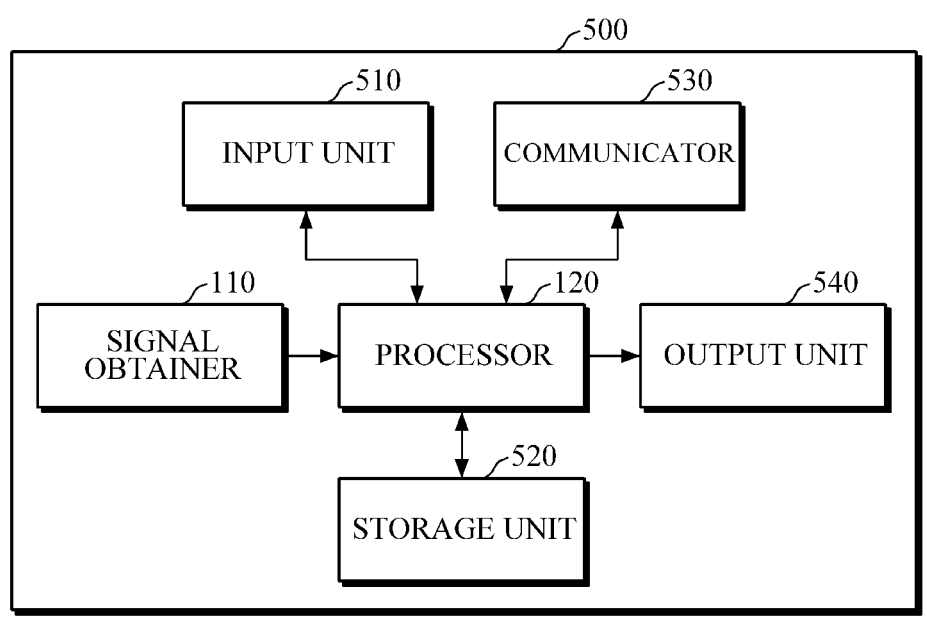
FIG. 5 is a block diagram illustrating another exemplary embodiment of a representative waveform providing apparatus.

FIG. 5 is a block diagram illustrating another exemplary embodiment of a representative waveform providing apparatus.

Referring to FIG. 5, the representative waveform providing apparatus 500 includes a signal obtainer 110, a processor 120, an input unit 510, a storage unit 520, a communicator 530, and an output unit 540. Here, the signal obtainer 110 and the processor 120 may be the same as those described with reference to FIG. 1, and thus detailed descriptions thereof will be omitted.

The input unit 510 may receive various operation signals from a user. According to an exemplary embodiment, the input unit 510 may include a key pad, a dome switch, a touch pad (e.g., resistive and/or capacitive type), a jog switch, a hardware (H/W) button, and the like. In particular, when the touch pad forms a mutual layer structure with a display, the touch pad may be referred to as a touch screen.

The storage unit 520 may store a program or instructions for operations of the representative waveform providing apparatus 500 and may store data input to and/or output from the representative waveform providing apparatus 500. In addition, the storage unit 520 may store periodic signal data obtained through the signal obtainer 110 and representative waveform data of the periodic signal determined by the processor 120.

The storage unit 520 may include at least one type of a storage medium, such as a flash memory, a hard disk, a micro type multimedia card, and a card type memory (e.g., secure digital (SD) or extreme digital (XD) memory), a random access memory (RAM), a static random access memory (SRAM), a read only memory (ROM), an electrically erasable programmable read only memory (EE-PROM), a programmable read only memory (PROM), a magnetic memory, a magnetic disk, an optical disk, or the like. In addition, the representative waveform providing apparatus 500 operates an external storage medium, such as a web storage, which performs the storage function of the storage unit 520 on the Internet.

The communicator 530 may communicate with an external device. For example, the communicator 530 may transmit data input from the user through the input unit 510, the periodic signal data obtained through the signal obtainer 110, representative waveform data of the periodic signal determined by the processor 120, and the like to the external device, or may receive various data that may be used to determine the representative waveform from the external device.

In this case, the external device may be a medical device that uses the obtained periodic signal data and/or the representative waveform of the periodic signal, a printer for outputting a result, or a display device which displays the obtained periodic signal data or the representative waveform of the periodic signal. In addition, the external device may be a digital television (TV), a desktop computer, a mobile phone, a smartphone, a tablet computer, a notebook computer, a PDA, a PMP, a navigation system, an MP3 player, a digital camera, a wearable device, or the like, but is not limited thereto.

The communicator 530 may use various communication technologies, such as Bluetooth communication, Bluetooth low energy (BLE) communication, near-field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, 5G communication, or the like. However, these are merely examples, and the communication technologies are not limited thereto.

The output unit 540 may output the periodic signal data and/or the representative waveform of the periodic signal. According to an exemplary embodiment, the output unit 540 may output the periodic signal data and/or the representative waveform of the periodic signal in at least one of audible, visual, or tactile manners. To this end, the output unit 540 may include a display, a speaker, a vibrator, and the like.

Figure 6:
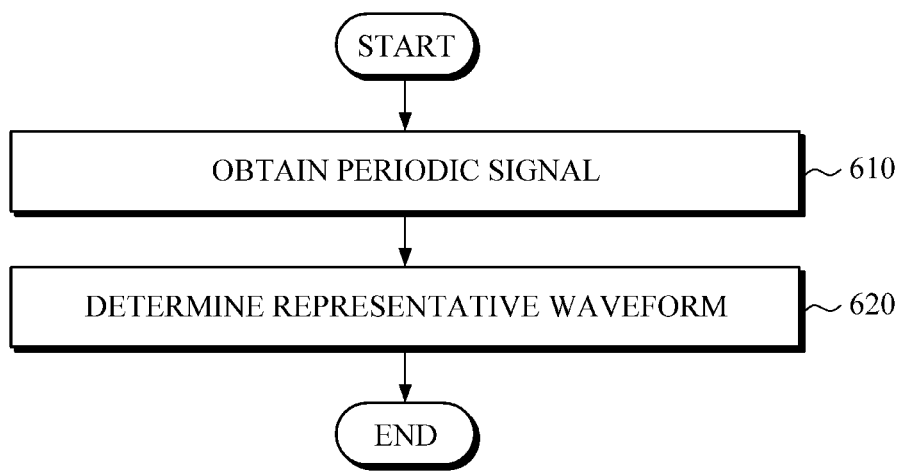
FIG. 6 is a flowchart illustrating an exemplary embodiment of a representative waveform providing method.

FIG. 6 is a flowchart illustrating an exemplary embodiment of a representative waveform providing method.

Referring to FIGS. 1 and 6, the representative waveform providing apparatus 100 obtains a periodic signal, in operation 610. For example, the representative waveform providing apparatus 100 may obtain the periodic signal from an external device which senses and/or stores periodic signals, or may obtain the periodic signal by using a PPG sensor, an ECG sensor, a BCG sensor, or the like.

The representative waveform providing apparatus 100 determines a representative waveform of the periodic signal by using a DTW algorithm, in operation 620.

Figure 7:
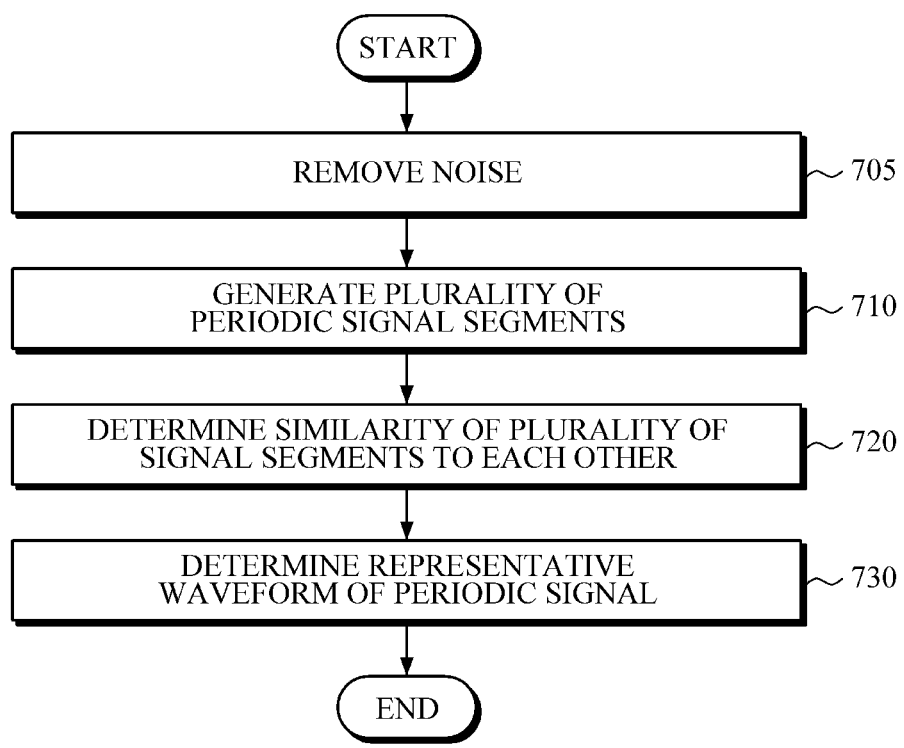
FIG. 7 is a flowchart illustrating an exemplary embodiment of an operation of determining a representative waveform.

FIG. 7 is a flowchart illustrating an exemplary embodiment of operation 620 of determining the representative waveform.

Referring to FIGS. 1 and 7, the representative waveform providing apparatus 100 generates a plurality of periodic signals by segmenting a periodic signal according to periods, in operation 710.

The representative waveform providing apparatus 100 determines a similarity of a plurality of periodic signals to each other using a DTW algorithm, in operation 720.

The representative waveform providing apparatus 100 determines the representative waveform based on the similarity between the periodic signals to each other, in operation 730.

According to an exemplary embodiment, the representative waveform providing apparatus 100 may select one periodic signal segment having the highest similarity to other periodic signal segments and may determine the selected periodic signal segment as the representative waveform.

According to another exemplary embodiment, the representative waveform providing apparatus 100 may select a specific number of periodic signal segments having high similarities to other periodic signal segments from among the plurality of periodic signal segments, obtain an ensemble average of the selected periodic signal segments to obtain an ensemble-averaged signal, and determine the obtained ensemble-averaged signal as the representative waveform.

According to still another exemplary embodiment, the representative waveform providing apparatus 100 may select two or more periodic signal segments whose similarities to other periodic signal segments are greater than a predetermined threshold from among the plurality of periodic signal segments, obtain an ensemble average of the two or more selected periodic signal segments to obtain an ensemble-averaged signal, and determine the obtained ensemble-averaged signal as the representative waveform.

The representative waveform providing apparatus 100 may remove noise from the periodic signal, in operation 705, before operation 710.

Figure 8:
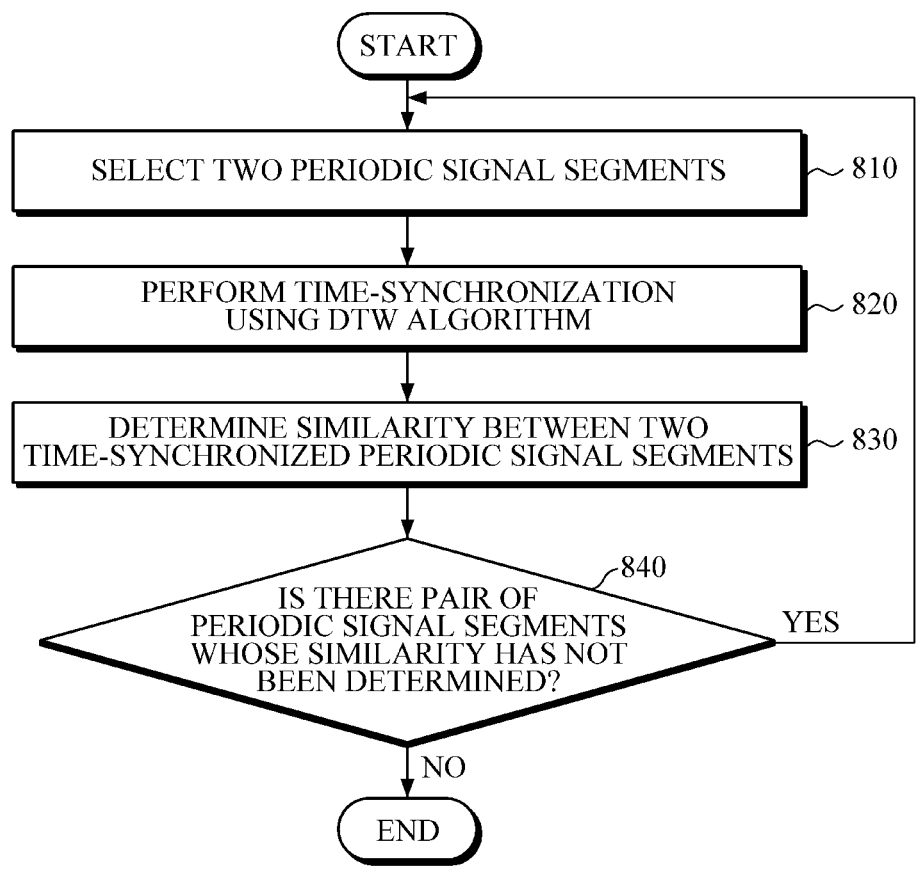
FIG. 8 is a flowchart illustrating an exemplary embodiment of an operation of determining a similarity of a plurality of periodic signal segments to each other.

FIG. 8 is a flowchart illustrating an exemplary embodiment of operation 720 of determining the similarity of the plurality of periodic signal segments to each other.

Referring to FIGS. 1 and 8, the representative waveform providing apparatus 100 selects two periodic signal segments from among the plurality of periodic signal segments, in operation 810.

The representative waveform providing apparatus 100 time-synchronizes the two periodic signal segments by applying the DTW algorithm to the two periodic signal segments to maximize the similarity between the two periodic signal segments, in operation 820. For example, the representative waveform providing apparatus 100 may time-synchronize the two periodic signal segments through the operations described above with reference to FIG. 4.

The representative waveform providing apparatus 100 determines the similarity between the two time-synchronized periodic signal segments, in operation 830. For example, the representative waveform providing apparatus 100 may determine the similarity between the two time-synchronized periodic signal segments by using at least one of correlation, signal difference, and an accumulated distance of an optimal path obtained in the process of time-synchronization.

The representative waveform providing apparatus 100 determines whether there are periodic signal segments in pair whose similarity has not been determined, in operation 840, and selects two periodic signal segments whose similarity has not been yet determined, in operation 810. Subsequent operations 820-840 may be repeated until it is determined that there are no periodic signal segments in pair whose similarity has not been determined.

Figure 9:
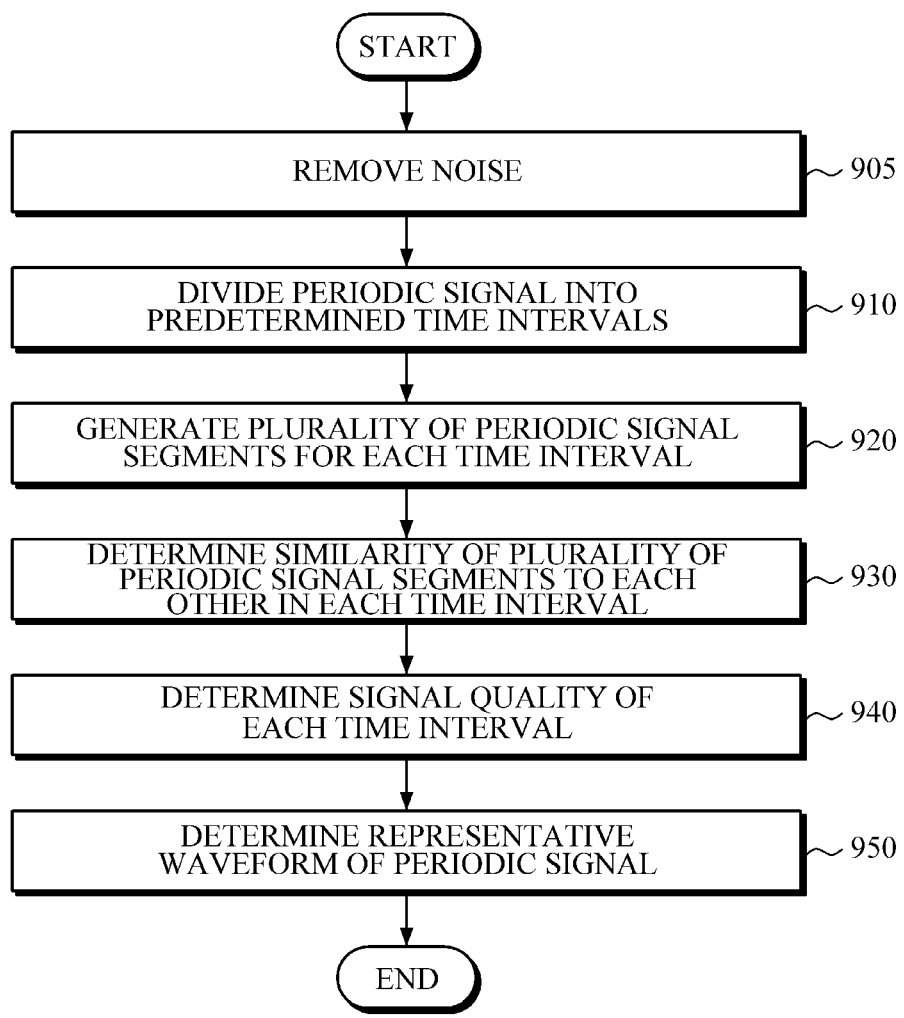
FIG. 9 is a flowchart illustrating another exemplary embodiment of an operation of determining a representative waveform.

FIG. 9 is a flowchart illustrating another exemplary embodiment of operation 620 of determining a representative waveform.

Referring to FIGS. 1 and 9, the representative waveform providing apparatus 100 divides the periodic signal into predetermined time intervals, in operation 910.

The representative waveform providing apparatus 100 generates a plurality of periodic signal segments by segmenting the periodic signal according to periods, in operation 920.

The representative waveform providing apparatus 100 may determine a similarity of the periodic signal segments to each other in each time interval using a DTW algorithm, in operation 930.

The representative waveform providing apparatus 100 determines a quality of the periodic signal of each time interval based on the similarity of the periodic signal segments to each other in each time interval, in operation 940. For example, the representative waveform providing apparatus 100 may determine that the quality of the periodic signal of a specific time interval is high when the similarity among the periodic signal segments of the corresponding time interval is high and determine that the quality of the periodic signal of a specific time interval is low when the similarity among the periodic signal segments of the corresponding time interval is low.

The representative waveform providing apparatus 100 determines the representative waveform of the periodic signal based on the signal quality determination result of the periodic signal of each time interval and the similarity of the periodic signal segments to each other in each time interval, in operation 950.

According to an exemplary embodiment, the representative waveform providing apparatus 100 may select a time interval having the highest signal quality, select one periodic signal segment having the highest similarity to other periodic signal segments from among the periodic signal segments of the selected time interval, and determine the selected periodic signal segment as the representative waveform.

According to another exemplary embodiment, the representative waveform providing apparatus 100 may select a time interval having the highest signal quality, select a predetermined number of periodic signal segments having high similarities to other periodic signal segments from among the periodic signal segments in the selected time interval, ensemble average the selected periodic signal segments to obtain an ensemble-averaged signal, and determine the obtained ensemble-averaged signal as the representative waveform.

According to still another exemplary embodiment, the representative waveform providing apparatus 100 may select a time interval having the highest signal quality and select two or more periodic signal segments whose similarities to other periodic signal segments are greater than a predetermined threshold from among the periodic signal segments in the selected time interval, ensemble average the two or more selected periodic signal segments to obtain an ensemble-averaged signal, and determine the obtained ensemble-averaged signal as the representative waveform.

According to yet another exemplary embodiment, the representative waveform providing apparatus 100 may select one periodic signal segment having the highest similarity to other periodic signal segment from among the periodic signal segments for each time interval, ensemble average the selected periodic signal segments of each time interval to obtain an ensemble-averaged signal, and determine the ensemble-averaged signal as the representative waveform. In this case, the representative waveform providing apparatus 100 may apply a different weight to the periodic signal segment selected for each time interval according to a signal quality of each time interval.

The representative waveform providing apparatus 100 may remove noise from the periodic signal, in operation 905, before operation 910.

Figure 10:
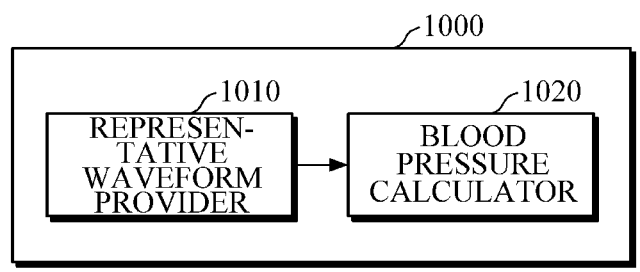
FIG. 10 is a block diagram illustrating an exemplary embodiment of a blood pressure estimation apparatus.

FIG. 10 is a block diagram illustrating an exemplary embodiment of a blood pressure estimation apparatus.

The blood pressure estimation apparatus 1000 of FIG. 10 may be implemented as a software module, a hardware module, and/or a combination thereof. For example, the blood pressure estimation apparatus 1000 may be provided in the form of a hardware chip and mounted on an electronic device. In this case, the electronic device may include a mobile phone, a smart phone, a notebook computer, a PDA, a PMP, a navigation system, an MP3 player, a digital camera, a wearable device, etc., and the wearable device may include various types of wearable devices, such as a wristwatch type, a wristband type, a ring type, a belt-type, a necklace type, an ankle band type, a thigh band type, a forearm band type, and the like. However, the electronic device is not limited to the above mentioned examples, and the wearable device is also not limited to the above-described examples.

Referring to FIG. 10, the blood pressure estimation apparatus 1000 includes a representative waveform provider 1010 and a blood pressure calculator 1020.

The representative waveform provider 1010 may obtain a PPG signal and determine a representative waveform of the PPG signal by using a DTW algorithm. The representative waveform provider 1010 may include at least one of the representative waveform providing apparatuses 100 and 500 described with reference to FIGS. 1 to 5, and detailed description thereof will be omitted.

The blood pressure calculator 1020 may obtain a blood pressure based on the representative waveform of the PPG signal determined by the representative waveform provider 1010. For example, the blood pressure calculator 1020 may obtain the blood pressure by analyzing the representative waveform of the PPG signal through pulse wave analysis (PWA).

Figure 11:
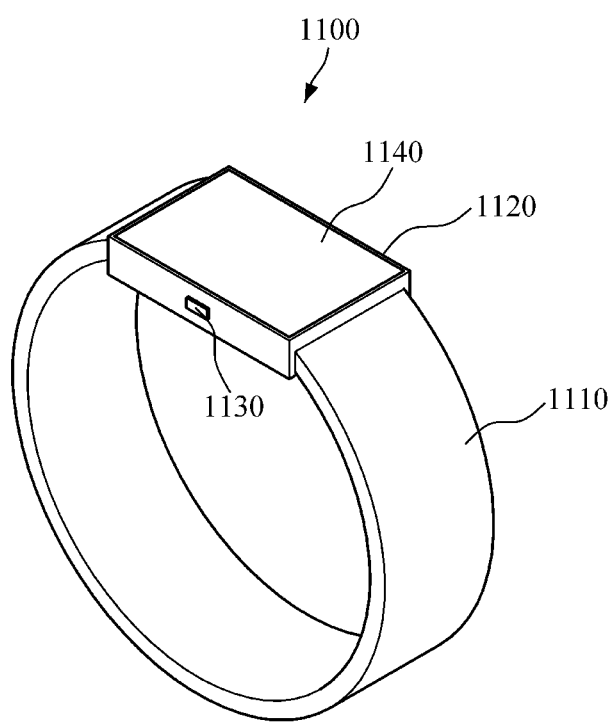
FIG. 11 is a perspective view of a wrist wearable device according to an exemplary embodiment.

FIG. 11 is a perspective view of a wrist wearable device according to an exemplary embodiment.

Referring to FIG. 11, the wrist wearable device 1100 includes a strap 1110 and a main body 1120.

The strap 1110 may be configured in the form of a flexible band. However, this is merely an exemplary embodiment, and the type of strap 1110 is not limited to the flexible band. That is, the strap 1110 may include a plurality of strap members configured to be bent in such a manner that each strap member is wrapped around the user's wrist.

The main body 1120 may include at least one of the above-described representative waveform providing apparatuses 100 and 500 or the blood pressure estimation apparatus 1000 mounted thereon. In addition, a battery for supplying power to the wrist wearable device 1100 may be installed inside the main body 1320.

The wrist wearable device 1100 may further include an input unit 1130 and a display 1140 which are mounted on the main body 1120. The input unit 1130 may receive various operation signals from a user. The display 1140 may display data processed by the wrist wearable device 1100, processing result data, and the like.

The exemplary embodiments may be implemented as computer readable codes in a computer readable record medium. Codes and code segments constituting the computer program may be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

At least one of the components, elements, modules or units represented by a block as illustrated in the drawings may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

The "unit" or "module" used herein may be a hardware component such as a processor or a circuit, and/or a software component that is executed by a hardware component such as a processor.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

Although a few exemplary embodiments have been shown and described, it would be appreciated by those skilled in the art that changes may be made in the exemplary embodiments without departing from the principles and spirit of the disclosure, the scope of which is defined in the claims and their equivalents.

What is claimed is:

1. A representative waveform providing apparatus, comprising:
   a signal obtainer configured to obtain a periodic signal; and
   a processor configured to determine a representative waveform of the periodic signal by using a dynamic time warping (DTW) algorithm,
   wherein the processor comprises:
      a signal segmentator configured to generate a plurality of periodic signal segments by segmenting the periodic signal according to periods;
      a similarity determiner configured to compare the plurality of periodic signal segments to each other using the DTW algorithm; and
      a representative waveform determiner configured to determine the representative waveform of the periodic signal based on a result of the comparison, and
   wherein a bio-signal corresponding to the periodic signal is generated based on the determined representative waveform, and
   wherein the bio-signal is a blood pressure signal.

2. The representative waveform providing apparatus of claim 1, wherein the periodic signal comprises a first periodic signal whose period does not change over time and a second periodic signal whose period gradually changes with time.

3. The representative waveform providing apparatus of claim 1, wherein the similarity determiner is configured to time-synchronize each pair of two periodic signal segments by applying the DTW algorithm to the two periodic signal segments in each pair and compare the two time-synchronized periodic signal segments in each pair.

4. The representative waveform providing apparatus of claim 1, wherein the representative waveform determiner is configured to determine the representative waveform based on a periodic signal segment having a highest correlations to other periodic signal segments among the plurality of periodic signal segments.

5. The representative waveform providing apparatus of claim 1, wherein the representative waveform determiner is configured to select a predetermined number of periodic signal segments whose correlations to other periodic signal segments from among the plurality of periodic signal segments are greater than a predetermined threshold from among the plurality of periodic signal segments, obtain an ensemble average of the selected predetermined number of periodic signal segments, and determine the representative waveform based on the obtained ensemble average.

6. The representative waveform providing apparatus of claim 1, wherein the representative waveform determiner is configured to select two or more periodic signal segments whose correlations to other periodic signal segments are greater than a predetermined threshold from among the plurality of periodic signal segments, obtain an ensemble average of the two or more selected periodic signal segments, and determine the representative waveform based on the obtained ensemble average.

7. The representative waveform providing apparatus of claim 1, wherein the processor comprises:
an interval divider configured to divide the periodic signal into predetermined time intervals;
a signal segmentator configured to generate a plurality of periodic signal segments for each time interval by segmenting the periodic signal in each time interval according to periods;
a similarity determiner configured to compare the plurality of periodic signal segments to each other in each time interval using the DTW algorithm; and
a representative waveform determiner configured to determine a signal quality value of each time interval based on a result of the comparison, and determine the representative waveform of the periodic signal based on results of determining the signal quality value and the comparison.

8. The representative waveform providing apparatus of claim 3, wherein the similarity determiner is configured to compare the time-synchronized two periodic signal segments by using at least one of correlation, signal difference, and an accumulated distance of an optimal path obtained in a process of the time-synchronization.

9. The representative waveform providing apparatus of claim 7, wherein the representative waveform determiner is configured to determine a signal quality value of a time interval based on the comparison of the plurality of periodic signal segments to each other in the corresponding time interval.

10. The representative waveform providing apparatus of claim 7, wherein the representative waveform determiner is configured to determine the representative waveform based on a periodic signal segment having at least one of highest correlation, smallest signal difference, and smallest accumulated distance of an optimal path obtained to other periodic signal segments among the plurality of periodic signal segments in a time interval having a highest signal quality value among the predetermined time intervals included in the periodic signal.

11. The representative waveform providing apparatus of claim 7, wherein the representative waveform determiner is configured to select a periodic signal segment having a highest correlation to other periodic signal segment from among the periodic signal segments included in each of the predetermined time intervals, ensemble average the selected periodic signal segments of each of the predetermined time intervals to obtain an ensemble-averaged signal, and determine the representative waveform based on the ensemble-averaged signal.

12. The representative waveform providing apparatus of claim 11, wherein the representative waveform determiner is configured to ensemble average the selected periodic signal segments by applying a different weight to the periodic signal segment selected for each of the predetermined time intervals according to a signal quality value of each of the predetermine time intervals.

13. A representative waveform providing method, comprising:
obtaining a periodic signal; and
determining a representative waveform of the periodic signal by using a dynamic time warping (DTW) algorithm,
wherein the determining of the representative waveform of the periodic signal comprises:
generating a plurality of periodic signal segments by segmenting the periodic signal according to periods;
comparing the plurality of periodic signal segments to each other by using the DTW algorithm; and
determining the representative waveform of the periodic signal based on a result of the comparing;
generating a bio-signal corresponding to the periodic signal based on the determined representative waveform, the bio-signal being a blood pressure signal.

14. The representative waveform providing method of claim 13, wherein the determining of the representative waveform of the periodic signal comprises determining the representative waveform based on a periodic signal segment having a highest correlation to other periodic signal segments among the plurality of periodic signal segments.

15. The representative waveform providing method of claim 13, wherein the determining of the representative waveform of the periodic signal comprises:
selecting a predetermined number of periodic signal segments having correlations to other periodic signal segments are greater than a predetermined threshold from among the plurality of periodic signal segments;
obtaining an ensemble average of the selected predetermined number of periodic signal segments to obtain an ensemble-averaged signal; and
determining the representative waveform based on the obtained ensemble-averaged signal.

16. The representative waveform providing method of claim 13, wherein the determining of the representative waveform of the periodic signal comprises:
selecting two or more periodic signal segments whose correlations to other periodic signal segments are greater than a predetermined threshold from among the plurality of periodic signal segments;
obtaining an ensemble average of the two or more selected periodic signal segments to obtain an ensemble-averaged signal; and
determining the representative waveform based on the obtained ensemble-averaged signal.

17. The representative waveform providing method of claim 13, wherein the determining of the representative waveform of the periodic signal comprises:
dividing the periodic signal into predetermined time intervals;
generating a plurality of periodic signal segments for each of the predetermined time intervals by segmenting the periodic signal in each of the predetermined time intervals according to periods;

determining a correlation of the plurality of periodic signal segments to each other in each of the predetermined time intervals by using the DTW algorithm;

determining a signal quality value of each of the predetermined time intervals based on a result of the determining the correlation; and determining the representative waveform of the periodic signal based on results of the determining the signal quality value and the correlation.

18. The representative waveform providing method of claim 17, wherein the determining the representative waveform of the periodic signal based on the results of the determining the signal quality value and the correlation comprises determining the representative waveform based on a periodic signal segment having a highest correlation to other periodic signal segments among the plurality of periodic signal segments in a time interval having a highest signal quality value among the predetermined time intervals included in the periodic signal.

19. The representative waveform providing method of claim 17, wherein the determining the representative waveform of the periodic signal based on the results of the determining the signal quality value and the correlation comprises:

selecting a periodic signal segment having a highest correlation to other periodic signal segment from among the periodic signal segments for each of the predetermined time intervals;

ensemble averaging the selected periodic signal segments by applying a different weight to the periodic signal segment selected for each of the predetermined time intervals according to a signal quality value of each of the predetermined time intervals; and determining the representative waveform based on the ensemble-averaged signal.

* * * * *